United States Patent [19]

Kronenthal

[11] Patent Number: 4,632,985
[45] Date of Patent: Dec. 30, 1986

[54] 3-ACYLAMINO-2-OXO-1-AZETIDINESULFONIC ACIDS

[75] Inventor: David Kronenthal, Yardley, Pa.

[73] Assignee: E. R. Squibb & Sons, Inc., Princeton, N.J.

[21] Appl. No.: 740,605

[22] Filed: Jun. 3, 1985

[51] Int. Cl.$^4$ .................. C07D 401/14; C07D 401/12; C07D 417/14; C07D 413/14
[52] U.S. Cl. .................................... 540/355; 546/261; 546/275; 546/277; 546/278
[58] Field of Search ..................... 260/245.4; 546/275; 346/280

[56] References Cited

FOREIGN PATENT DOCUMENTS 2071650 9/1981 United Kingdom .

OTHER PUBLICATIONS

Abstracts of the 1984 ICAAC meeting, "Antimicrobial Activities of 1-Carbacephem Compounds and Their Structure-Activity Relationships", Mochida et al.

*Primary Examiner*—Mark L. Berch
*Attorney, Agent, or Firm*—Lawrence S. Levinson; Donald J. Barrack

[57] ABSTRACT

Antibacterial activity is exhibited by 2-azetidinones activated in the 1-position with an —SO$_3$H group and having in the 3-position an acylamino group of the formula

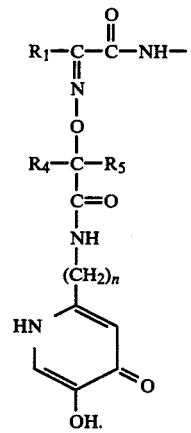

11 Claims, No Drawings

3-ACYLAMINO-2-OXO-1-AZETIDINESULFONIC ACIDS

BRIEF DESCRIPTION OF THE INVENTION

Compounds having the formula

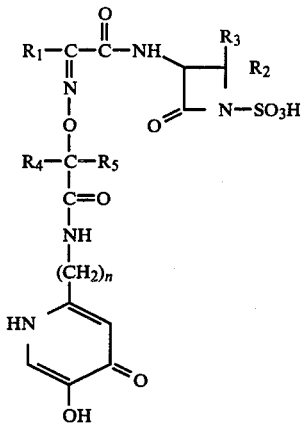

and pharmaceutically acceptable salts thereof, have antibacterial activity. In formula I, and throughout the specification, the symbols are as defined below.

$R_1$ is phenyl, substituted phenyl, 2-amino-4-thiazolyl, 5-amino-3-(1,2,4-thiadiazolyl), 2-amino-4-oxazolyl, 2-amino-4-imidazolyl, or 2-amino-6-pyridyl;

$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_a$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino (—$NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

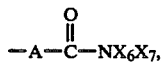

—S—$X_2$, or —O—$X_2$ (wherein A, $X_2$, $X_6$ and $X_7$ are as hereinafter defined)], —S—$X_2$ or —O—$X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

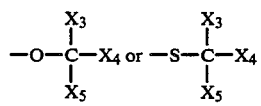

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

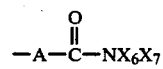

(substituted amino)carbonyl, or cyano (-C≡N)], or $$-A-\overset{O}{\underset{\|}{C}}-NX_6X_7$$

wherein A is —CH=CH—, —$(CH_2)_m$—, —$(CH_2)_m$—O—, —$(CH_2)_m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle];

$R_4$ and $R_5$ are the same or different and each is hydrogen or alkyl or $R_4$ and $R_5$ together with the carbon atom to which they are attached are cycloalkyl; and n is 0 or 1.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "cycloalkyl" refers to cycloalkyl groups having 3,4,5,6 or 7 carbon atoms.

The term "substituted alkyl" refers to alkyl groups substituted with one or more (preferably 1, 2 or 3) azido, amino (—$NH_2$), halogen, hydroxy, carboxy, cyano, alkoxycarbonyl, aminocarbonyl, alkanoyloxy, alkoxy, phenyloxy, (substituted phenyl)oxy, $R_a$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—$NH_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4,5,6 or 7-membered heterocycle" (referred to as "$R_a$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

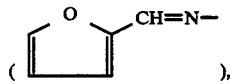

benzylideneamino and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihyrothiazolyl and hexahydroazepinyl. Exemplary of the substituted 4,5,6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —$NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy, or amino (—$NH_2$).

The compounds of this invention form basic salts with inorganic and organic bases which are also within the scope of this invention. Such salts include ammonium salts, alkali metal salts, alkaline earth metal salts, and salts with organic bases such as dicyclohexylamine, benzathine, N-methyl-D-gluccamine, hydrabamine and the like.

The compounds of this invention are pictured as acids. They can also exist, however, as zwitterions (internal or inner salts), and these are also included within the language "pharmaceutically acceptable salts" and the scope of this invention.

DETAILED DESCRIPTION OF THE INVENTION

The β-lactams of formula I, and pharmaceutically acceptable salts thereof, have activity against gram-positive and gram-negative organisms. Of particular interest is the good antipseudomonal activity exhibited by the compounds of this invention. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The compounds of this invention wherein n is 1 can be prepared by coupling a compound having the formula

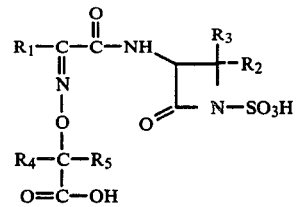

II with a nucleophile having the formula

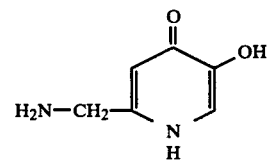

III

The coupling reaction can be run using procedures well known in the art. Exemplary of such procedures are the dicyclohexylcarbodiimide coupling and the dicyclohexylcarbodiimide/N-hydroxybenzotriazole coupling.

The compounds of this invention wherein n is 0 or 1 can be prepared by condensing a glyoxylic acid having the formula

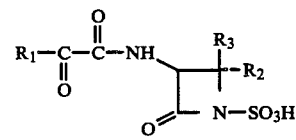

IV with an alkoxylamine having the formula

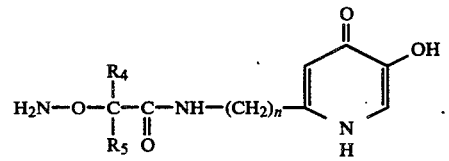

V

The condensation reaction can be run in water, an organic solvent, or a mixed organic solvent-water system.

Another procedure for preparing the compounds of this invention wherein n is 0 or 1 comprises coupling a carboxylic acid having the formula

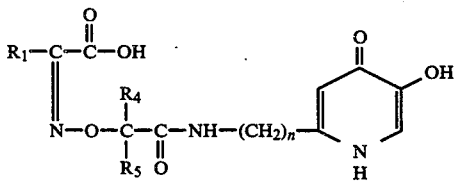

VI with a β-lactam having the formula

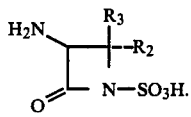

The reaction proceeds most readily if the carboxylic acid is in an activated form. Activated forms of carboxylic acids are well known in the art and include acid halides, acid anhydrides (including mixed anhydrides), activated acid amides and activated acid esters.

The β-lactams of formulas II, IV and VII can be prepared using the methodology described in United Kingdom patent application No. 2,071,650, published Sept. 23, 1981.

The starting material of formula III (i.e., 2-(aminomethyl)-5-hydroxy-4-oxo-1,4-dihydropyridine) can be prepared from 2-(hydroxymethyl)-5-hydroxy-4H-pyran-4-one using the methodology set forth in parts A-E of Exmaple 1, infra.

A starting material of formula V can be prepared by first reacting a phthalimide having the formula

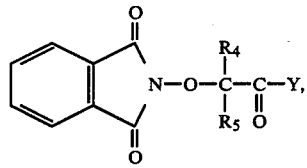

wherein Y is a halogen or hydroxyl group, with a compound of formula III or the compound having the formula

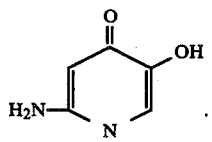

When Y is hydroxyl, the reaction proceeds best in the presence of a coupling agent such as dicyclohexylcarbodiimide. The phthalimide protecting group is then removed using hydrazine or methylhydrazine. Amine protecting groups other than the phthalimide group can also be used in preparing a compound of formula V.

The compound of formula IX (i.e., 2-amino-5-hydroxy-4-oxo-1,4-dihydropyridine) can be prepared from 5-(benzyloxy)-2-(hydroxymethyl)-4H-pyran-4-one using the methodology set forth in parts A-F of Example 2, infra.

A carboxylic acid reactant of formula VI can be prepared by reacting a compound having the formula

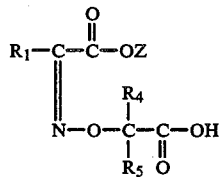

with a compound of formula III or IX. Alternatively, a glyoxylic having the formula

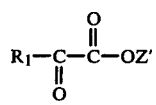

can be reacted with a compound of formula V to yield the desired reactant of formula VI. As used above, the symbol "Z" represents a carboxylic acid protecting group and "Z'" represents hydrogen or a carboxylic acid protecting group. The carboxylic acids of formula VI are an integral part of this invention.

In the above reactions, if the $R_1$ group contains an amino substituent, it may be protected; exemplary protecting groups are the triphenylmethyl and formyl groups. Also, the hydroxyl group on the pyridinone nucleus (or hydroxyl groups on the tautomer) can be protected. Exemplary protecting groups are the trimethylsilyl, benzyl and benzyhydryl groups.

Those compounds of formula I wherein $R_1$ is 2-amino-4-thiazolyl are preferred. In the case of $R_4$ and $R_5$, methyl is in the preferred alkyl group.

The compounds of formula I contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

Compounds of formula I exists as tautomeric mixtures. The two forms are as shown below:

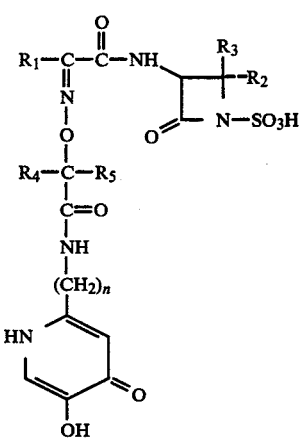

-continued

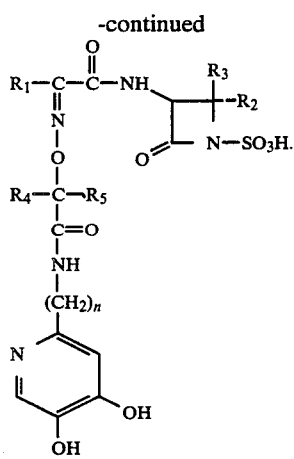

The tautomeric products are obtained in relative amounts that differ from compound to compound. Both forms are included within the scope of structural formula I.

The compounds of formula I have the imino substituent

and can, therefore, exist as the syn or anti isomer or as a mixture of isomers. All of these isomeric forms are within the scope of this invention. In general, however, the syn isomer of a compound of formula I has the greatest activity.

Exemplary of the compounds falling within the scope of this invention are:

[3S-[3α(Z),4β]]-3-[[(2-amino-4-thiazolyl)[2-[[(1,4-dihydro-5-hydroxy-4-oxo-2-pyridinyl)methyl]amino]-1,1-dimethyl-2-oxoethoxy]imino]acetyl]amino]-4-methyl-2-oxo-1-azetidinesulfonic acid

[3S-[3α(Z),4β]]-3-[[(2-amino-4-thiazolyl)[2-[[(1,4-dihydro-5-hydroxy-4-oxo-2-pyridinyl)methyl]amino]-1,1-dimethyl-2-oxoethoxy]imino]acetyl]amino]-4-[[(carbamoyl)oxy]methyl]-2-oxo-1-azetidinesulfonic acid

[3S(Z)]-3-[[(2-amino-4-thiazolyl)[2-[[(1,4-dihydro-5-hydroxy-4-oxo-2-pyridinyl)methyl]amino]-1,1-dimethyl-2-oxoethoxy]imino]acetyl]amino]-2-oxo-1-azetidinesulfonic acid

[3S-[3α(Z),4α]]-3-[[(2-amino-4-thiazoly)[2-[[(1,4-dihydro-5-hydroxy-4-oxo-2-pyridinyl)methyl]amino]-1,1-dimethyl-2-oxoethoxy]imino]acetyl]amino]-4-methyl-2-oxo-1-azetidinesulfonic acid

[3S-[3α(Z),4β]]-3-[[(2-amino-4-thiazolyl)[[2-[(1,4-dihydro-5-hydroxy-4-oxo-2-pyridinyl)amino]-1,1-dimethyl-2-oxoethoxy]imino]acetyl]amino]-4-methyl-2-oxo-1-azetidinesulfonic acid

[3S-[3α(Z),4β]]-3-[[(2-amino-4-thizolyl)[[2-[(1,4-dihydro-5-hydroxy-4-oxo-2-pyridinyl)amino]-1,1-dimethyl-2-oxoethoxy]imino]acetyl]amino]-4-[[(carbamoyl)oxy]methyl]-2-oxo-1-azetidinesulfonic acid

[3S(Z)]-3-[[(2-amino-4-thiazolyl)[[2-[(1,4-dihydro-5-hydroxy-4-oxo-2-pyridinyl)amino]-1,1-dimethyl-2-oxoethoxy]imino]acetyl]amino]-2-oxo-1-azetidinesulfonic acid

[3S-[3α(Z),4α]]-3-[[(2-amino-4-thiazolyl)[[2-[(1,4-dihydro-5-hydroxy-4-oxo-2-pyridinyl)amino]-1,1-dimethyl-2-oxoethoxy]imino]acetyl]amino]-4-methyl-2-oxo-1-azetidinesulfonic acid The following examples are specific embodiments of this invention.

EXAMPLE 1

[3S-[3α(Z),4β]]-3-[[(2-Amino-4-thiazolyl)[[2-[[(1,4-dihydro-5-hydroxy-4-oxo-2-pyridinyl)methyl]amino]-1,1-dimethyl-2-oxoethoxy]imino]acetyl]amino]-4-methyl-2-oxo-1-azetidinesulfonic acid, monopotassium salt

(A)

2-(Hydroxymethyl)-5-[(phenylmethyl)oxy]-4H-pyran-4-one

A suspension of 2-(hydroxymethyl)-5-hydroxy-4H-pyran-4-one (56.8 g, 0.4 mole) in 400 ml of methanol was treated with sodium hydroxide (16 g, 0.4 mole) in 200 ml of warm methanol followed by 50.6 g (46 ml, 0.4 mole) of benzyl chloride. The mixture was heated to reflux for 3.5 hours, cooled, and poured into 1 L of water. The resulting solid was filtered and washed with ca. 1.5 L of water, 200 ml of ethanol and 400 ml of hexane. After drying under high vacuum, the weight of product was 55.7 g.

(B)

2-(Hydroxymethyl)-5-[(phenylmethyl)oxy]-4-oxo-1,4-dihydropyridine

A mixture of 2-(hydroxymethyl)-5-[(phenylmethyl)oxy]-4H-pyran-4-one (9.65 g, 41.59 mmole), 95 ml of concentrated ammonia and 20 ml of ethanol were heated at reflux overnight. An additional 75 ml of ammonium hydroxide was added, the mixture was refluxed for 2 hours and cooled. The resulting brown solid was filtered and washed with water until the washings were neutral. The crude product was suspended in ethanol, filtered, washed with ethanol and hexane and dried in vacuo. The yield of the title compound was 7.61 g.

(C)

2-(Chloromethyl)-5-[(phenylmethyl)oxy]-4-oxo-1,4-dihydropyridine hydrochloride

A suspension of 2-(hydroxymethyl)-5-[(phenylmethyl)oxy]-4-oxo-1,4-dihydropyridine (3 g, 12.99 mmole) in chloroform (15 ml) was cooled to 0° C. under argon and treated with thionyl chloride (6.1 ml, 83.62 mmole). Within several minutes, a homogeneous solution was obtained. After stirring an additional 5 minutes, a cream colored solid precipitated. The cooling bath was removed, and the mixture was heated at reflux for 45 minutes. The mixture was cooled to 0° C. and the white suspended material was filtered, washed with chloroform and hexane and dried in vacuo. The yield of the title compound was 3.65 g.

(D)

2-(Azidomethyl)-5-[(phenylmethyloxy)]-4-oxo-1,4-dihydropyridine

A mixture of 2-(chloromethyl)-5-[(phenylmethyl)oxy]-4-oxo-1,4-dihydropyridine hydrochloride (3.59 g, 12.54 mmole), sodium azide (4.08 g, 62.7 mmole) and diisopropylethylamine (2.19 ml, 12.54 mmole) in 70 ml of dimethylformamide was stirred at room temperature under argon for 3.5 days. An additional 4.08 g of sodium azide was added, and the mixture was heated at 45°-50° C. for 2 hours. After cooling, the reaction was poured into 500 ml of water, producing an insoluble white solid.

The pH of the supernatant liquid was lowered from 8.5 to 7.5 with dilute hydrochloric acid, and the white solid was filtered. After washing with water, acetone, and hexane, the solid was dried in vacuo. The yield of the title compound was 2.81 g.

(E)
2-(Aminomethyl)-5-hydroxy-4-oxo-1,4-dihydropyridine

A suspension of 2-(azidomethyl)-5-[(phenylmethyloxy)]-4-oxo-1,4-dihydropyridine (641 mg, 2.5 mmole) in 7 ml of dimethylformamide was treated with p-toluenesulfonic acid monohydrate (951 mg, 5 mmole), and the resulting solution was treated with 10% palladium on charcoal (641 mg). The mixture was stirred under 1 atmosphere of hydrogen for 75 minutes. The hydrogen was purged with argon, and diisopropylethylamine (871 μl, 5 mmole) was added. The resulting mixture was used immediately in the following reaction.

(F)
[3S-[3α(Z),4β]]-3-[[(2-Amino-4-thiazolyl)[[2-[[(1,4-dihydro-5-hydroxy-4-oxo-2-pyridinyl)methyl]amino]-1,1-dimethyl-2-oxoethoxy]imino]acetyl]amino]-4-methyl-2-oxo-1-azetidinesulfonic acid, monopotassium salt A solution of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid (1.09 g, 2.5 mmole) in 5 ml of dimethylformamide was treated with N,N-diisopropylethylamine (436 μl, 2.5 mmole) and added to the dimethylformamide solution containing 2-(aminomethyl)-5-hydroxy-4-oxo-1,4-dihydropyridine. Dicyclohexylcarbodiimide (516 mg, 2.5 mmole) was added, and the reaction was stirred overnight at room temperature under argon. The insolubles were filtered, the filter cake was washed with dimethylformamide and the filtrate was concentrated under high vacuum. The residue was treated with water, filtered, and the filter cake was washed with water (total filtrate volume ca. 200 ml). After refiltration, the aqueous solution was lyophilized. The lyophilate was dissolved in 20% acetone:water and chromatographed on Dowex ion-exchange resin (K+ form, 150 ml). Fractions 9–12 (14 ml fractions) were combined and lyophilized. The lyophilate (1.2 g) was purified on HP-20 (500 ml); fractions 1–20 were eluted with water, fractions 21–41 with 5% acetone:water. Fractions 35–36 were combined and lyophilized to produce 129 mg (8.7%) of SQ 30,204. An additional 60 mg of material was obtained from fractions 37–39.

Analysis Calc'd for $C_{19}H_{22}N_7O_9S_2K.2.78\ H_2O$: C, 35.35; H, 4.30; N, 15.19. Found: C, 35.35; H, 4.55; N, 14.99.

EXAMPLE 2
[3S-[3α(Z),4β]]-3-[[(2-Amino-4-thiazolyl)[[2-[[(1,4-dihydro-5-hydroxy-4-oxo-2-pyridinyl]amino]-1,1-dimethyl-2-oxoethoxy]imino]acetyl]amino]-4-methyl-2-oxo-1-azetidinesulfonic acid, monopotassium salt A 5-(Benzyloxy)-1,4-dihydro-4-oxo-2-pyridine carboxylic acid A mixture of 5-(benzyloxy)-4-pyrone-2-carboxylic acid (10.92 g, 44.4 mmole) in 35 ml of 95% ethanol and 70 ml of ammonium hydroxide was refluxed for 6 hours. The volatiles were removed in vacuo, the residue was dissolved in water and the pH was lowered to 3 with HCl. The resulting solid was filtered and washed with water. Recrystallization from methanol afforded 9.5 g of the title compound.

(B)
5-(Benzyloxy)-1,4-dihydro-4-oxo-2-pyridinecarboxylic acid, ethyl ester

A suspension of 5-(benzyloxy)-1,4-dihydro-4-oxo-2-pyridinecarboxylic acid (8.24 g, 33.6 mmole) in 120 ml of ethanol was cooled to 0° C. and treated with a stream of dry HCl for 15 minutes. The resulting mixture was heated at 50° C. for 5.5 hours. The volatiles were removed in vacuo and the residue was treated with water. While cooling, the pH was raised to 7 with saturated potassium bicarbonate and the resulting mixture was extracted with dichloromethane. The extracts were washed with brine and dried over sodium sulfate. Filtration and concentration in vacuo produced 7.32 g of the title compound.

(C)
5-(Benzyloxy)-2-(hydrazinocarbonyl)-4-oxo-1,4-dihydropyridine

A suspension of 5-(benzyloxy)-1,4-dihydro-4-oxo-2-pyridinecarboxylic acid, ethyl ester (7.1 g, 26 mmole) in 99% hydrazine hydrate (15 ml) was heated until most of the solid dissolved. The resulting mixture was stirred for 25 minutes at ambient temperature, the excess hydrazine was removed under high vacuum and the solid residue was treated with methanol. The volatiles were removed in vacuo (repeat methanol treatment and evaporation twice), the solid residue was washed with methanol, hexane, and dried to afford 6 g of the title compound.

(D)
2-(Azidocarbonyl)-5-(benzyloxy)-4-oxo-1,4-dihydropyridine

A solution of concentrated hydrochloric acid (3 ml) in water (10 ml) was cooled to 0° C. and treated with 5-(benzyloxy)-2-(hydrazinocarbonyl)-4-oxo-1,4-dihydropyridine (3 g, 11.58 mmole) to form a thick paste. A solution of sodium nitrite (1.68 g, 23.17 mmole) in water (30 ml) was added in 2 ml portions with mechanical swirling of the reaction vessel. The resulting mixture was stirred for 3.5 hours and filtered. The resulting pasty solid was washed with water, ice-cold ethanol, ether and hexane. After drying thoroughly under high vacuum, the yield of the title compound was 2.6 g.

(E)
5-(Benzyloxy)-1,4-dihydro-4-oxo-2-pyridinecarbamic acid, benzyl ester

Benzyl alcohol (80 ml) was heated to 95° C. (oil bath temperature) under argon and treated with 2-(azidocarbonyl)-5-(benzyloxy)-4-oxo-1,4-dihydropyridine (2.6 g, 9.1 mmole) in small portions. The temperature of the oil bath was raised to 110° C. and heating was continued for 2.5 hours. The mixture was cooled and concentrated in vacuo. Ethyl acetate was added, the resulting solid was washed with ethyl acetate, hexane, and dried in vacuo to yield 1.5 g of the title compound.

(F)
2-[(1,3-Dihydro-1,3-dioxo-2H-indol-2-yl)oxy]-N-[5-(benzyloxy)-1,4-dihydro-4-oxo-2-pyridinyl]-2-methylpropanamide A solution of 5-(benzyloxy)-1,4-dihydro-4-oxo-2-pyridinecarbamic acid, benzyl ester (635 mg, 1.81 mmole) in dimethylformamide (5 ml) was treated sequentially with p-toluenesulfonic acid hydrate (691 mg, 3.63 mmole) and 10% palladium on charcoal and stirred under hydrogen (1 atm.) at room temperature for 2 hours. The dimethylformamide was removed in vacuo and the residue was treated with dichloromethane (12 ml), cooled to 0° C., and treated with N-methyl-N-(trimethylsilyl)trifluoroacetamide (MSTFA; 5 ml, 27.21 mmole). The resulting mixture was stirred at 0° C. for 30 minutes and treated with a solution of 2-[(1,3-dihydro-1,3-dioxo-2H-indol-2-yl)oxy]-2-methylpropanecarbonyl chloride (485 mg, 1.81 mmole) in dichloromethane (4 ml). The reaction was stirred at 0° C. for 2 hours, warmed to room temperature, and stirred overnight. The catalyst was filtered off, the volatiles were removed in vacuo (toluene used to chase MSTFA) and the residue was dissolved in dichloromethane, cooled to 0° C., and treated with methanol. The cooling bath was removed and the mixture was stirred at room temperature for 20 minutes. The volatiles were removed in vacuo, the residue was treated with water, and the pH was raised to 6 with potassium bicarbonate solution. The resulting mixture was applied to a Diaion HP-20 column (200 ml) with dimethylformamide. Elution with acetone:water (25% for 350 ml, then 50%) produced 220 mg of the title compound as a white powder.

(G)
2-(Aminooxy)-N-[(5-benzyloxy)-1,4-dihydro-4-oxo-2-pyridinyl]-2-methylpropanamide A suspension of 2-[(1,3-dihydro-1,3-dioxo-2H-indol-2-yl)oxy]-N-[5-(benzyloxy)-1,4-dihydro-4-oxo-2-pyridinyl]-2-methylpropanamide (50 mg, 0.15 mmole) in 95% ethanol (0.5 ml) was cooled to 0° C. under argon and treated with hydrazine hydrate (9 μl). The mixture was stirred at 0° C. for 30 minutes, warmed to room temperature, stirred for 1 hour, and then refluxed for 2.5 hours. The reaction was cooled, filtered, and concentrated in vacuo to produce 18 mg of the title compound.

(H)
[3S-[3α(Z),4β]]-3-[[(2-Amino-4-thiazolyl)[[2-[[(1,4-dihydro-5-hydroxy-4-oxo-2-pyridinyl]amino]-1,1-dimethyl-2-oxoethoxy]imino]acetyl]amino]-4-methyl-2-oxo-1-azetidinesulfonic acid, monopotassium salt A mixture of 2-(aminooxy)-N-[(5-benzyloxy)-1,4-dihydro-4-oxo-2-pyridinyl]-2-methylpropanamide and (3S-trans)-3-[[(2-amino-4-thiazolyl)(oxoacetyl)]amino]-4-methyl-2-oxo-1-azetidinesulfonic acid, monopotassium salt (29 mg) in water is stirred at pH 4.0 for 36 hours. The pH is raised to 4.5 with potassium bicarbonate solution and the mixture is lyophilized. Chromatography of the lyophillate on Diaion HP-20 resin affords the title compound.

What is claimed is:
1. A compound having the formula

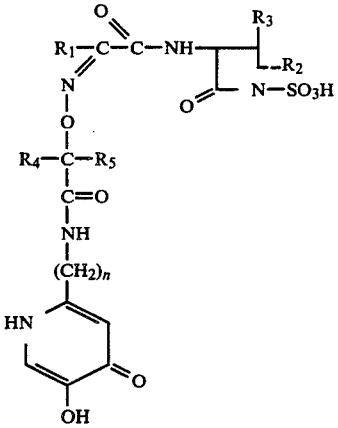

or a pharmaceutically acceptable salt thereof, wherein
R$_1$ is phenyl, substituted phenyl, 2-amino-4-thiazolyl, 5-amino-3-(1,2,4-thiadiazolyl), 2-amino-4-oxazolyl, 2-amino-4-imidazolyl, or 2-amino-6-pyridyl;

R$_2$ and R$_3$ are the same or different and each is hydrogen, alkyl, alkenyl, alkynyl, cycloalkyl, phenyl, substituted phenyl or a 4, 5, 6 or 7-membered heterocycle or one of R$_2$ and R$_3$ is hydrogen and the other is azido, halomethyl, dihalomethyl, trihalomethyl, alkoxycarbonyl, 2-phenylethenyl, 2-phenylethynyl, carboxyl,

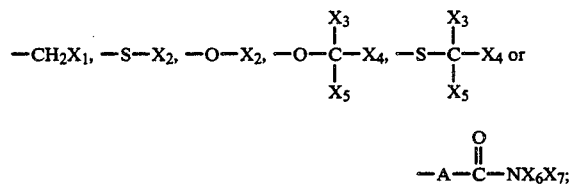

$$-A-\overset{O}{\underset{\|}{C}}-NX_6X_7;$$

R$_4$ and R$_5$ are the same or different and each is hydrogen or alkyl, or R$_4$ and R$_5$ together with the carbon atom to which they are attached are cycloalkyl;

n is 0 or 1;

X$_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano, $$-A-\overset{O}{\underset{\|}{C}}-NX_6X_7,$$

—S—X$_2$, or —O—X$_2$;

X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl;

one of X$_3$ and X$_4$ is hydrogen and the other is hydrogen or alkyl, or X$_3$ and X$_4$ when taken together with the carbon atom to which they are attached form a cycloalkyl group;

X$_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

$X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

A is $-CH=CH-$, $-(CH_2)_m-$, $-(CH_2)_m-O-$, $-(CH_2)_m-NH-$ or $-CH_2-S-CH_2-$; and m is 0, 1 or 2; and wherein the terms "alkyl" and "alkoxy" refer to groups having 1 to 10 carbon atoms;

the term "cycloalkyl" refers to groups having 3, 4, 5, 6 or 7 carbon atoms;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the terms "alkanoyl", "alkenyl" and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbons, alkoxy of 1 to 4 carbons, alkanoyloxy, aminocarbonyl, or carboxy groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazoyl, triazinyl, tetrazolyl, azetidinyl, oxetanyl, thietanyl, piperidinyl, piperazinyl, imidazolidinyl, oxazolidinyl, pyrrolidinyl, tetrahydropyrimidinyl, dihydrothiazolyl, hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups; and the term "substituted amino" refers to a group having the formula $-NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy, or amino.

2. A compound in accordance with claim 1 wherein $R_2$ and $R_3$ are the same or different and each is hydrogen or alkyl.

3. A compound in accordance with claim 1 wherein $R_2$ and $R_3$ are the same or different and each is hydrogen or methyl.

4. A compound in accordance with claim 1 wherein one of $R_2$ and $R_3$ is hydrogen and the other is methyl.

5. A compound in accordance with claim 1 wherein $R_1$ is 2-amino-4-thiazolyl.

6. A compound in accordance with claim 1 wherein n is 0.

7. A compound in accordance with claim 1 wherein n is 1.

8. A compound in accordance with claim 1 wherein $R_4$ and $R_5$ are each hydrogen.

9. A compound in accordance with claim 1 wherein $R_4$ and $R_5$ are each methyl.

10. A compound in accordance with claim 1 wherein $R_4$ is hydrogen and $R_5$ is methyl.

11. The compound in accordance with claim 1 [3S-3α(Z), 4β]]-3-[[(2-amino-4-thiazolyl)[[2-[[(1,4-dihydro-5-hydroxy-4-oxo-2-pyridinyl)methyl]amino]-1,1-dimethyl-2-oxoethoxy]imino]acetyl]amino]-4-methyl-2-oxo-1-azetidinesulfonic acid, or a pharmaceutically acceptable salt thereof.

* * * * *

UNITED STATES PATENT AND TRADEMARK OFFICE
CERTIFICATE OF CORRECTION

PATENT NO. : 4,632,985                    Page 1 of 2
DATED      : December 30, 1986
INVENTOR(S): David Kronenthal It is certified that error appears in the above-identified patent and that said Letters Patent is hereby corrected as shown below:

Please correct formula I in Column 1 to read as follows:

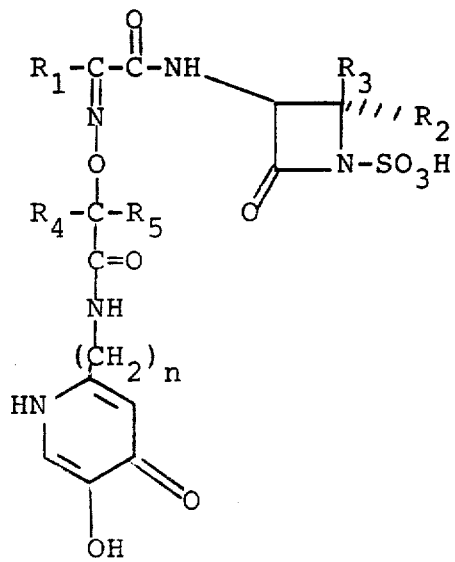

UNITED STATES PATENT AND TRADEMARK OFFICE
CERTIFICATE OF CORRECTION

PATENT NO. : 4,632,985

DATED : December 30, 1986

INVENTOR(S) : David Kronenthal

It is certified that error appears in the above-identified patent and that said Letters Patent is hereby corrected as shown below:

Column 2, line 8, delete the "s" following "-C".

Column 12, correct the formula of claim 1 to read as follows:

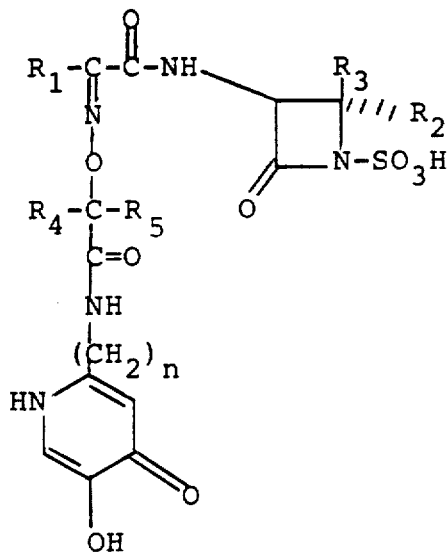

Signed and Sealed this

Fourteenth Day of April, 1987

*Attest:*

DONALD J. QUIGG

*Attesting Officer*     *Commissioner of Patents and Trademarks*